(12) United States Patent
Laubscher et al.

(10) Patent No.: US 8,665,431 B2
(45) Date of Patent: Mar. 4, 2014

(54) CUVETTE AND METHOD FOR AUTHENTICATING A CUVETTE

(75) Inventors: Markus Laubscher, Eindhoven (NL); Pim Theo Tuyls, Mol (BE); Milan Petkovic, Eindhoven (NL); Boris Skoric, S-hertogenbosch (NL)

(73) Assignee: Koninklijke Philips N.V., Eindhoven (NL)

( * ) Notice: Subject to any disclaimer, the term of this patent is extended or adjusted under 35 U.S.C. 154(b) by 241 days.

(21) Appl. No.: 13/126,329

(22) PCT Filed: Nov. 2, 2009

(86) PCT No.: PCT/IB2009/054859
§ 371 (c)(1),
(2), (4) Date: Jul. 15, 2011

(87) PCT Pub. No.: WO2010/052634
PCT Pub. Date: May 14, 2010

(65) Prior Publication Data
US 2011/0259091 A1    Oct. 27, 2011

(30) Foreign Application Priority Data
Nov. 6, 2008   (EP) .................................... 08168446

(51) Int. Cl.
*G01N 1/10* (2006.01)
(52) U.S. Cl.
USPC ........................................................ 356/246

(58) Field of Classification Search
None
See application file for complete search history.

(56) References Cited

U.S. PATENT DOCUMENTS

| 2003/0074223 A1 | 4/2003 | Hickle |
| 2007/0005367 A1 | 1/2007 | DeJean |

FOREIGN PATENT DOCUMENTS

| EP | 1475242 A1 | 11/2004 |
| EP | 1586379 A1 | 10/2005 |
| WO | 8809925 A1 | 12/1988 |
| WO | 9005903 A2 | 5/1990 |
| WO | 2006020363 A2 | 2/2006 |
| WO | 2006120643 A1 | 11/2006 |
| WO | 2007023420 A1 | 3/2007 |
| WO | 2007064596 A2 | 6/2007 |
| WO | 2007132184 A1 | 11/2007 |
| WO | 2008129123 A1 | 10/2008 |

*Primary Examiner* — Gregory J Toatley
*Assistant Examiner* — Amanda Merlino

(57) ABSTRACT

A cuvette (10) for storing a biological sample to be analyzed by means of a predefined detection technique is disclosed. The cuvette (10) is formed from a moldable material that contains particles (15a, 15b) at a concentration within a predefined range. The particles (15a, 15b) are randomly distributed, in order to form a unique pattern. Moreover, the particles (15a, 15b) have measurable physical properties, so that the unique pattern is detectable using the detection technique that is used to analyze the biological sample. The unique properties obtained by the randomly distributed particles (15a, 15b) render copying nearly impossible, since it is more complicated to distribute the particles in a predetermined pattern than to let them distribute randomly.

20 Claims, 2 Drawing Sheets

CUVETTE AND METHOD FOR AUTHENTICATING A CUVETTE

TECHNICAL FIELD

The present invention relates to a cuvette for storing a biological sample to be analyzed by a measuring device. The invention also relates to a method for authentication of a cuvette.

BACKGROUND OF THE INVENTION

In health care today an increasing amount of analysis of biological samples are performed instantly at the point of care due to for example developed techniques in this area. The increasing use of biological analysis causes usage of an increased amount of disposable cuvettes on which a biological sample, such as a blood sample, is stored. When performing the analysis the cuvette is introduced to a measuring device that generates an analysis result.

Low cost producers have noticed that the profit is made through selling such disposable cuvettes, rather than selling the actual measuring device to which a cuvette is introduced, whereby copying of cuvettes by low cost producers has become a problem. Cuvettes being produced by low cost producers impacts on the quality of cuvettes that leads to decreased reliability of analysis results when the copied cuvettes are used in measuring devices intended for the original cuvettes.

In an attempt to give a unique identity to a known cuvette it could be labeled with an identifier, such as a bar code. However, labeling requires additional steps in the manufacturing process and such a label is moreover relatively easy to reproduce. Therefore, there is a need for a cuvette that cannot be easily reproduced to thereby obtain reliable test results and that can be easily authenticated to its corresponding measuring device.

SUMMARY OF THE INVENTION

In view of the above mentioned need, a general object of the present invention is to provide a cuvette that cannot be easily reproduced, and which is adapted to be authenticated. This and other objects are achieved through a cuvette for storing a biological sample to be analyzed by means of a predefined detection technique, the cuvette being formed from a moldable material, such as a plastic material, containing particles at a concentration within a predefined range. The particles are randomly distributed, in order to form a unique pattern, and the particles have measurable physical properties, so that the unique pattern is detectable using the detection technique.

The unique pattern of the present invention is used as an identifier of the cuvette, and is integrated in the material from which the cuvette is formed, by means of randomly distributed particles. The unique properties obtained by the randomly distributed particles render copying nearly impossible, since it is more complicated to distribute the particles in a predetermined pattern than to let them distribute randomly.

Furthermore, the physical properties of the particles being measurable renders the unique pattern detectable, and by that means each cuvette holds a unique detectable identity. In addition, the pattern being detectable using the same detection technique as for detecting the biological sample forms a basis for a simple authentication of the cuvette using the same technique as when analyzing the biological sample. In other words, the cuvette of the present invention is less laborious to give the unique properties to, more complicated to copy than cuvettes of prior art, and adapted to easily be authenticated without requiring additional equipment.

The cuvette may moreover have a handle portion and an introducible portion adapted to be introduced into a measuring device, at least a portion of the introducible portion being a sample holding portion for storing of a biological sample, wherein the unique pattern is comprised in the introducible portion outside the sample holding portion with the result that the unique pattern may be introduced to a measuring device together with the biological sample. The unique pattern being separated from the sample holding portion forms a basis for a correct analysis result as well as a correctly executed authentication of the cuvette.

Further, the size of the particles may be in the order of micrometers, preferably ranging from 1 to 10 micrometers, such as micro beads, having the properties to be easily detected by detection techniques used for sample analysis. Furthermore, the particles may have such properties so that they easily distribute in the moldable material, which hence simplifies the manufacturing process, and the achievement of the unique pattern. An example of particle material is glass.

The cuvette may be provided with a readable label, wherein the label contains a stored digital representation of the unique pattern, which forms a basis for a reliable authentication of the cuvette, where the stored digital representation may be compared to the unique pattern of the cuvette.

The label may be readable using the same detection technique. In this case, the label is preferably arranged adjacent to the unique pattern, so that only one image is enough to both read the label and detect the unique pattern.

Further, the physical properties may be at least one of reflectivity and transmittivity, in which case the detection technique may be optical detection of an image. This is a suitable technique for obtaining a representation of the unique pattern and to read the stored representation of the label, which technique is also a common technique for analyzing a biological sample. Other detection techniques include for example chemical analysis.

According to a second aspect of the present invention there is provided a method for manufacturing a cuvette for storing a biological sample to be analyzed by means of a predefined detection technique. The method comprises the steps of providing a moldable material containing particles at a concentration within a predefined range, which particles have measurable physical properties; and forming a cuvette from the material, so that the particles are randomly distributed, in order to form a unique pattern, which is detectable using the detection technique.

Providing the particles constituting the unique properties already in the manufacturing process is a relatively simple way to achieve unique properties, since it belongs to the nature of such particles, such as micro beams, to distribute randomly in the moldable material. Moreover, as described in relation to the cuvette according to the present invention copying such a cuvette is nearly impossible, since it is much more complicated to manufacture a cuvette by inserting particles in a predetermined pattern, than to let them distribute randomly.

According to a third aspect of the present invention, there is provided a method for authenticating a cuvette formed from a moldable material comprising particles having measurable physical properties, the particles being randomly distributed, in order to form a unique, detectable pattern. The method comprises the steps of introducing the cuvette into a measuring device that is intended to analyze a biological sample, such as a blood sample; and detecting the unique pattern of the cuvette using the measuring device.

Re-using a measuring device that is intended for performing an analysis of a biological sample for also detecting the unique pattern of the cuvette is efficient and practical. No additional detection device is hence required for this purpose, and the effect of with certainty preventing usage of copied products in a measuring device is obtained.

When the cuvette is provided with a label comprising a stored digital representation of the unique pattern the method may further comprise the steps of reading the stored digital representation from the label to be verified; and comparing the stored digital representation with the detected unique pattern to thereby achieve a reliable result of authentication.

Moreover, the label may be readable using equipment used to detect the unique pattern, so as to be readable by the measuring device. In this case, the label is preferably provided adjacent to the unique pattern, so that only one image is enough to both read the label and detect the unique pattern.

BRIEF DESCRIPTION OF THE DRAWINGS

In the following, embodiments of the present invention will be described in detail, with reference to the accompanying, exemplifying drawings on which.

DETAILED DESCRIPTION OF PREFERRED EMBODIMENTS

Figure 1:
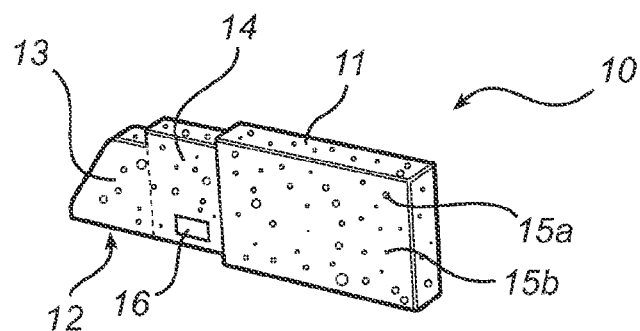
FIG. 1 is a perspective view of a cuvette and a measuring device according to the present invention.

The present invention will be mainly described hereinafter with reference to a cuvette 10 illustrated in FIG. 1.

The cuvette 10 is formed from a moldable material, e.g. a plastic material, that comprises particles 15a-b, such as glass micro beads, that are randomly distributed in the moldable material before the cuvette 10 is molded. The properties of the particles 15a-b are moreover measurable.

The cuvette 10 comprises a handle portion 11 and an introducible portion 12. The handle portion 11 of the cuvette 10 is adapted to be held by a user when storing a blood sample from a patient, and for simplifying insertion of the introducible portion 12 of the cuvette 10 into a measuring device. The introducible portion 12 of the cuvette 10 is further divided into a sample holding portion 13, where the blood sample is stored, and an authentication portion 14, adapted to uniquely identify the cuvette 10, by the properties achieved by particles 15a-b. The particles 15a-b form a unique pattern due to the unique location and orientation in relation to each other of these particles 15a-b for each cuvette 10. Since the properties of the particles 15a-b are measurable the unique pattern may be both detected and stored, for example by means of taking an image of the pattern. The unique pattern of the authentication portion 14 of the cuvette 10 is as mentioned dedicated for the purpose of identifying the cuvette.

There is a label 16 provided on the cuvette, that contains a stored digital representation of the unique pattern of the cuvette, and alternatively also a digital signature. In more detail the label may for example have been produced by first taking an image of the authentication portion 14 of the unique pattern, which image has been transformed into a compact digital representation. The signature has then been generated from the digital representation for example by means of using a signing algorithm. Signing may be performed by using for example a private key of a certification authority. The digital representation and the digital signature has thereafter been combined into so called enrolment data, which is printed or otherwise provided as a label 16 on the cuvette 10, in the form of for example a bar code, a block code, or an electronic identifier, such as an RFID. Alternatively, the digital representation is stored e.g. in a database in the device that performs the authentication method.

By digitally signing the digital representation it is more difficult for a malicious party to generate valid data, since it also requires a valid signature.

Figure 2:
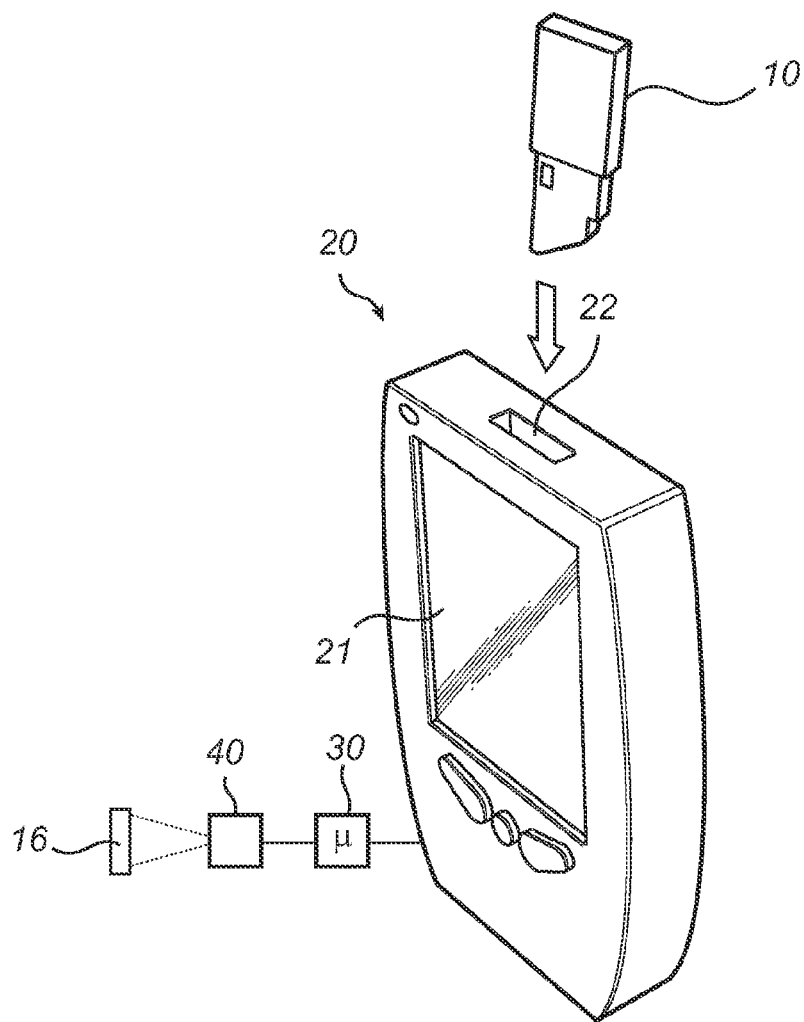
FIG. 2 is a perspective view of a system for analyzing a biological sample and for authenticating a cuvette.

In FIG. 2 a system for analyzing a blood sample that is stored on the cuvette and for authenticating the cuvette is illustrated. The system comprises a measuring device 20 intended to perform blood sample analysis, an authentication device 30 connected to the measuring device 20, and a reader 40 connected to the authentication device 30.

The measuring device 20 has a display 21 for displaying analysis data etc, and an opening 22 in which the cuvette 10 may be inserted. The measuring device 20 is intended for analyzing a blood sample, which is achieved through image detection techniques. As an alternative to optical detection of an image, the detection may be based on for example electrical or chemical techniques. In operation the cuvette 10 is inserted to the measuring device 20, whereby the unique pattern of the authentication portion 14 may be detected and the blood sample which is stored on the sample holding portion 13 of the cuvette 10 may be analyzed using the same detection technique, performed by the measuring device 20.

The reader 40 is adapted to read the label of the cuvette 10, and depending on the type of label 16, the reader 40 may be for example a bar code reader or a block code reader.

Figure 3:
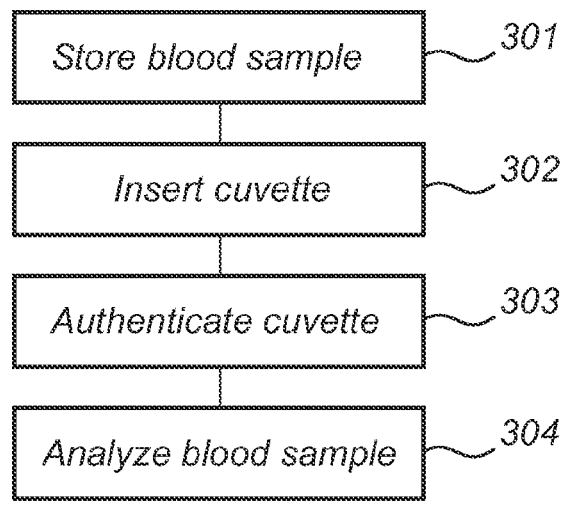
FIG. 3 is a flow chart schematically illustrating an exemplary method for analyzing a biological sample of the present invention.
Figure 4:
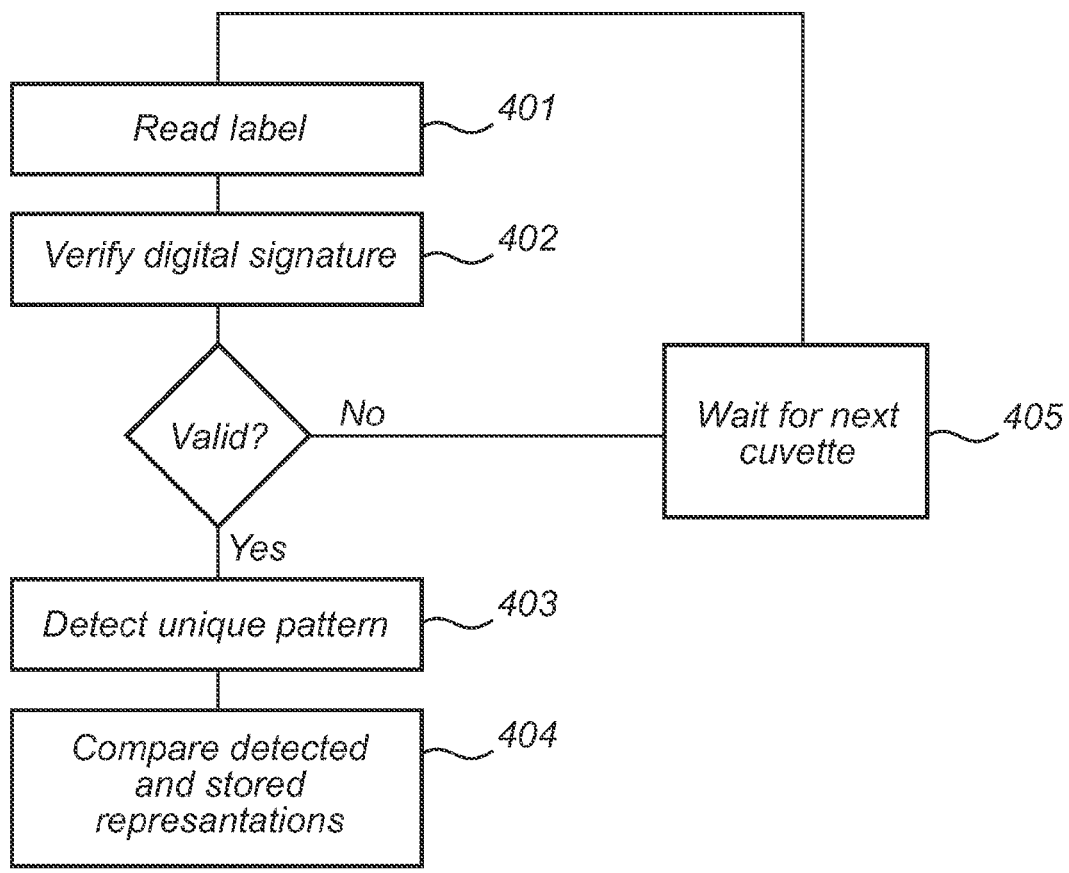
FIG. 4 is a flow chart schematically illustrating an exemplary method for authenticating a cuvette performed by the measuring device.

The authentication device 30 is arranged to receive data which is read by the reader 40 and to authenticate the cuvette 10 using this information, which is further described in relation to FIGS. 3 and 4. The authentication device 30 may be a micro processor.

Alternatively the reader 40 and the authentication device 30 are part of the measuring device.

An example of a method for analyzing a biological sample, here a blood sample, will now be described with reference to FIG. 3 which is a flow chart schematically illustrating such a method.

First, in step 301, a blood sample is taken from a patient at a point of care, and is stored at the sample holding portion of the cuvette 10. Thereafter, in step 302, the cuvette 10 is inserted to the opening 22 of the measuring device 20.

In step 303 the cuvette is authenticated by means of an authentication method that will be further described with reference to FIG. 4. If the authentication is successful, meaning that the cuvette 10 is an original cuvette that is to be used in the measuring device 20 in question, step 204 is performed.

In step 304 the blood sample is analyzed according to conventional methods performed by the measuring device 20.

An example of a method for authenticating a cuvette will now be described with reference to FIG. 4 which is a flow chart schematically illustrating such a method. The method may be implemented in the authentication device 30 by storing computer program code portions in the device 30, a processor controlling the method described hereinafter First, in step 401, the reader 40 reads the label 16 provided on the cuvette 10.

The digital signature and the digital representation are transmitted to the authentication device 30. Thereafter, in step 402, the authentication device 30 verifies the digital signature comprised in the label 16. The verification is performed by using the public key corresponding to the private key used when producing the digital signature. Only if this verification is valid, the next step 403 is performed, otherwise the program control proceeds to step 405, waiting for next cuvette to be verified.

In step 403, after a valid verification of the digital signature and the cuvette has been inserted into the measuring device 20, the unique pattern is detected for example by means of taking an image of the pattern from a designated authentication portion 14 outside the sample holding portion of the cuvette 10. A representation of the detected unique pattern is transmitted to the authentication device.

Next, in step 404, the digital representation that was read from the label 16 in step 301 is compared to the detected unique pattern, by the authentication device 30. If the consistency between these two is not sufficient the cuvette 10 is considered to be fake, and is not compatible with the measuring device 20 in question.

In case there is no digital signature the steps concerning the digital signature may accordingly be left out of the method.

Step 401 and 403 of reading the label 16 and detecting the unique pattern may moreover be executed at the same time, by the measuring device 20, if the properties of the cuvette 10 allow that the same technique is used for both reading the label and detecting the unique pattern, for example by taking an image using a microscope. This may be achieved by using a photoactive dye inside the cuvette 10 which can be modified with a laser. Moreover, it requires that the label 16 and the unique pattern 14 be arranged adjacent to each other.

The person skilled in the art realizes that the present invention is not limited to the preferred embodiments. For example the particle properties may be of any measurable kind, such as intensity, or color, the unique pattern may be measured by various detection techniques and combinations of these, such as only reflective measurements, or both reflective and transmission measurements, etc.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A cuvette for storing a biological sample to be analyzed by means of a predefined detection technique, said cuvette being formed from a moldable material containing particles at a concentration within a predefined range, said particles being randomly distributed forming a unique detectable pattern,
said particles having measurable physical properties.

2. The cuvette according to claim 1, having a handle portion and an introducible portion adapted to be introduced into a measuring device, at least a portion of said introducible portion being a sample holding portion for storing of said biological sample, wherein said unique detectable pattern is comprised in said introducible portion outside said sample holding portion.

3. The cuvette according to claim 1, wherein the size of said particles is in the order of micrometers.

4. The cuvette according to claim 1, timber provided with a readable label, wherein said label contains a stored digital representation of said unique detectable pattern.

5. The cuvette according to claim 4, wherein said label is readable using said detection technique, and arranged adjacent to said unique detectable pattern.

6. The cuvette according to claim 1, wherein the physical properties are at least one of reflectivity and transmittivity.

7. The cuvette according to claim 6, wherein said detection technique is optical detection of an image.

8. A method for manufacturing a cuvette for storing a biological sample to be analyzed by means of a predefined detection technique, comprising the steps of:
providing a moldable material containing particles at a concentration within a predefined range, which particles have measurable physical properties; and
forming a cuvette from said material, so that said particles are randomly distributed forming a unique detectable pattern.

9. The method for manufacturing a cuvette according to claim 8, further comprising the step of providing said cuvette with a readable label containing a stored digital representation of said unique detectable pattern.

10. The method of claim 9, wherein said label is provided adjacent to said unique detectable pattern, and is readable using said detection technique.

11. A method for authenticating a cuvette formed from a moldable material comprising particles having measurable physical properties, said panicles being randomly distributed forming a unique detectable pattern, which method comprises the steps of:
introducing the cuvette into a measuring device that is intended to analyze a biological sample; and
detecting the unique detectable pattern using said measuring device.

12. The method according to claim 11, wherein the cuvette is provided with a label, said label comprising a stored digital representation of the unique detectable pattern method further comprising the steps of
reading said stored digital representation from the label; and
comparing the stored digital representation with the detected unique detectable pattern.

13. A method for analyzing a biological sample by a measuring device, comprising the steps of:
storing a biological sample on a cuvette formed from a moldable material comprising panicles having measurable physical properties, said particles being randomly distributed forming a unique detectable pattern;
authenticating the cuvette; and
analyzing said biological sample with said measuring device.

14. A system for analyzing a biological sample comprising:
a measuring device adapted to analyze a biological sample stored on a cuvette and detect a unique detectable pattern formed from particles having measurable physical properties being randomly distributed in said cuvette; and
an authentication device adapted to receive information from the measuring device; and authenticate said cuvette based on said information.

15. The system according to claim 14, further comprising:
a reader adapted to read a label provided on said cuvette and storing a digital representation of the unique detectable pattern;
said authentication device further being adapted to receive information from the reader.

16. The system according to claim 14, wherein the size of said particles is in the order of micrometers.

17. The system according to claim 14, wherein the cuvette is provided with a readable label containing a stored digital representation of said unique detectable pattern.

18. The system according to claim 17, wherein said label is readable using a detection technique, and arranged adjacent to said unique detectable pattern.

19. The cuvette according to claim 14, wherein the physical properties are at least one of reflectivity and transmittivity.

20. The cuvette according to claim 18, wherein said detection technique is optical detection of an image.

\* \* \* \* \*